Figure 1:
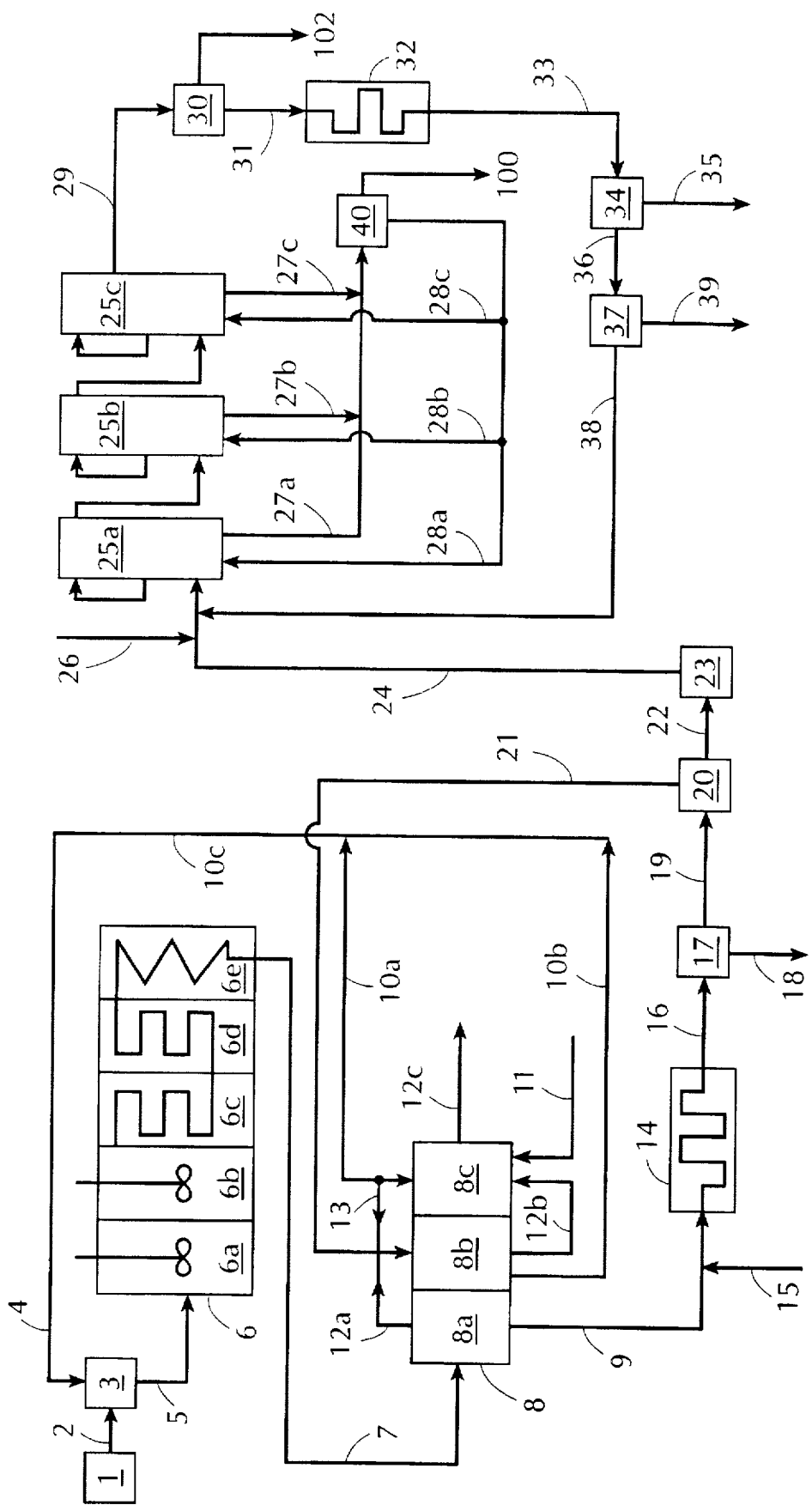

United States Patent [19]
Dziondziak et al.

[11] Patent Number: 5,762,991
[45] Date of Patent: Jun. 9, 1998

[54] CONTINOUS PROCESS OF PRODUCING BEER

[75] Inventors: Klaus Dziondziak, Pinneberg; Rudolf Bonsch, Nackenheim; Roland Herbert Bodmer, Nidderau; Michael Karl Hans Eichelsbacher, Mainz; Peter Mitschke, Maintal; Ulrich Heinrich Friedrich Sander, Friedrichsdorf; Eberhard Julius Friedrich Schlichting, Wehrheim, all of Germany

[73] Assignee: Metalgesellschaft Aktiengesellschaft, Frankfurt am Main, Germany

[21] Appl. No.: 481,310

[22] PCT Filed: Dec. 17, 1993

[86] PCT No.: PCT/EP93/03601

§ 371 Date: Aug. 14, 1995

§ 102(e) Date: Aug. 14, 1995

[87] PCT Pub. No.: WO94/16054

PCT Pub. Date: Jul. 21, 1994

[30] Foreign Application Priority Data

Dec. 31, 1992 [DE] Germany ............ 42 44 595.7
Dec. 31, 1992 [DE] Germany ............ 42 44 596.5
Dec. 31, 1992 [DE] Germany ............ 42 44 597.3

[51] Int. Cl.⁶ .............. C12L 7/00; C12L 11/07; C12L 11/09; C12L 12/04
[52] U.S. Cl. .............. 426/11; 426/14; 426/16; 426/28; 426/29; 426/30; 426/492; 426/493; 426/592
[58] Field of Search .............. 426/11, 14, 16, 426/28, 29, 592, 30, 493, 492

[56] References Cited

U.S. PATENT DOCUMENTS

| | | | |
|---|---|---|---|
| 3,989,848 | 11/1976 | Moll et al. | 426/30 |
| 3,993,791 | 11/1976 | Breed et al. | 426/436 |
| 4,388,857 | 6/1983 | Korek | 99/276 |
| 4,550,029 | 10/1985 | Kruger et al. | 426/487 |
| 4,552,060 | 11/1985 | Redl et al. | 99/278 |
| 4,564,595 | 1/1986 | Neves | 435/163 |
| 4,681,066 | 7/1987 | Widhopf | 122/234 |
| 4,801,462 | 1/1989 | Tonna | 426/16 |
| 4,882,177 | 11/1989 | Dziondziak | 426/14 |
| 4,946,784 | 8/1990 | Sander | 435/178 |
| 4,978,545 | 12/1990 | Cutayar et al. | 426/312 |
| 5,114,491 | 5/1992 | Sarhaddar | 127/38 |
| 5,453,285 | 9/1995 | Versteegh | 426/29 |
| 5,536,650 | 7/1996 | Versteegh | 435/93 |

FOREIGN PATENT DOCUMENTS

| | | |
|---|---|---|
| 0245845 | 11/1987 | European Pat. Off. |
| 1804343 | 5/1970 | Germany |
| 289765 | 5/1971 | Germany |
| 3704478 | 7/1988 | Germany |
| 4142646 | 11/1992 | Germany |

OTHER PUBLICATIONS

Kontinuierliche Brauverfahren * Heutiger Stand Und Ansätze für Morgen, Dipl.-Ing. (FH) Peter Kollnberger, Brauindustrie Jun. 1991, pp. 514–520.

An Engineering Approach To Continuous Brewing, by Lars Ehnstrom, Food Engineering Int'l., Dec. 1976, pp. 22–27.

Hochtemperatur-Würzekochung Und Würzebehandlung, by Von S. Julin und H. Berger, Glinde, Brauwelt 15, 12 Apr. 1979, pp. 492–494.

*Primary Examiner*—David L. Lacey
*Assistant Examiner*—Curtis E. Sherrer
*Attorney, Agent, or Firm*—Felfe & Lynch

[57] ABSTRACT

A continuous process of producing beer is described. Starch-containing raw materials are disintegrated and are optionally processed to form malt, a wort is produced from the disintegrated and optionally malted raw materials, and the wort is subjected to alcoholic fermentation. In that process all process steps are performed continuously. The mash is initially heated in a reactor system to a temperature of 75° to 85° C. The grain residue is removed from the mash. The wort is subsequently hopped and is heated to a temperature from 105° to 140° C. This is succeeded by a flash evaporation, a removal of the dregs and a cooling of the wort, which is subsequently fermented at 6° to 25° in the presence of a biocatalyst. The fermenting process may be succeeded by a partial or full continuous de-alcoholization of the beer.

22 Claims, 3 Drawing Sheets

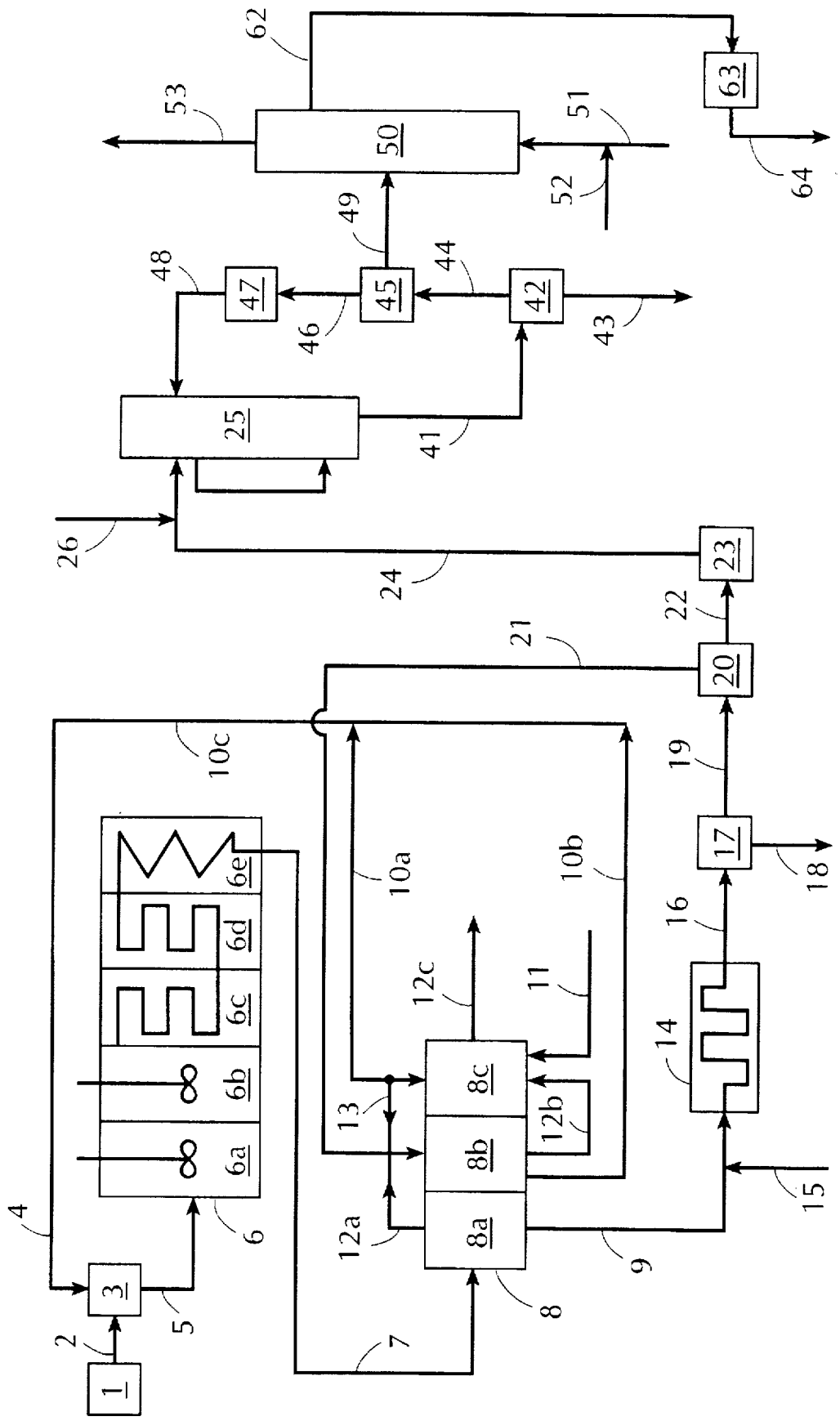

CONTINOUS PROCESS OF PRODUCING BEER

BACKGROUND OF INVENTION

This invention relates to a process of producing beer, wherein starch-containing raw materials are disintegrated and are optionally processed to form malt, a wort is produced from the disintegrated and optionally malted raw materials, and the wort is subjected to alcoholic fermentation. Beer is a generic term for all beverages produced from starch-containing raw materials by alcoholic fermentation. After the fermentation, a part of the alcohol can be removed from the beer. Alcohol-containing beer (draft beer or strong beer) contains more than 2.5% by volume alcohol. Low-alcohol beer contains less than 2.5% by volume and preferably less than 1% by volume alcohol, and non-alcoholic beer contains less than 0.05% by volume alcohol.

Starch-containing raw materials cannot be fermented directly but must previously be saccharified by an activity of hydrolytic enzymes (amylases, proteases, glucanases). By the saccharification the starch is converted to dextrins and fermentable sugars. The malt usually employed to produce beer is generally derived from suitable kinds of barley in that the barley is initially germinated at 15° to 18° C. for several days and the germinated barley is subsequently dried at temperatures up to 100° C. In the malt from which dust and germs have been removed a part of the starch is already in the form of dextrins and maltose and salt malt also contains native hydrolytic enzymes, which during the preparation of the wort complete the saccharification of the starch. That malt is disintegrated and the disintegrated malt is mashed with water and is treated at 35° to 75° C. to complete the saccharification and to dissolve the dextrins and the fermentable sugars. After the insoluble constituents (grain residue) have been removed, the wort is boiled. Before and/or during the boiling the sort is flavored with hops or hop extract. After the grain residue has been removed and the hopped wort has been cooled, the oxygen required for the fermentation is added and the fermentation is performed at 6° to 20° C. for several days. An afterfermenation is effected at −2° to 3° C. The beer is then filtered and $CO_2$ is optionally added. If unmalted cereals or other starch-containing raw materials are used rather than malt, the saccharification will be effected in special cases in that the starch-containing ground raw materials are mixed with water and are subsequently digested with non-native hydrolytic enzymes and are thus converted to dextrins and fermentable sugars.

All process stages of the beer production are normally carried out by a batch processing. To improve the economy of the production of beer, a semicontinuous or continuous brewing has already been proposed. The continuous production of beer with the aid of immobilized yeast cells has intensely been studied for some years but has again and again been criticized for being not entirely satisfactory for various reasons.

publication by P. Kollnberger, Brauindustrie June 1991, pages 514 to 520, gives a general review on continuous brewing processes and arrives at the result that complete plants for a continuous production of beer have not been disclosed thus far because the production of beer depends on such a large number of factors that a complete continuous process would not be justified.

In the publication by L. Ehnstrom, Food Engineering int'l, December 1976, pages 22 to 27, a continuous process of producing sort is disclosed in Which the raw materials are ground in a dry state to a particle size from 100 to 500 micrometers and mashing is effected in a tubular reactor, in which lautering is effected by a countercurrent extraction in a plurality of separators and boiling is effected in that steam at 140° to 150° C. is directly injected under pressure and this is followed by a pressure relief into a vacuum to a temperature of 65° to 95° C.

The publication by S. Julin and H. Berger, Brauwelt 15, 1979, pages 492 to 494, proposes a high-temperature boiling of the wort. In three spiral heat exchangers the hopped wort is heated in steps to a temperature of about 140° C. and after passing through a reaction path, in which a holding at an elevated temperature is ensured for 5 minutes, the wort is pressure-relieved to ambient pressure in two stages whereafter the boiled wort is at a temperature of about 100° C.

It is apparent that the publications by Julin and Berger and by Ehnstrom disclose partial processes for a continuous production of beer but fail to propose how the continuous production of wort can be integrated in a continuous fermenting and ripening process.

Published German Application 18 04 343 relates to an apparatus for separating the wort from the grain residue. That apparatus essentially consists of a mash tub and two succeeding extractors. Each extractor is divided into front and rear chambers and the mash is continuously conveyed from the mash tub through the extractors to the means for discharging the grain residue. It is not apparent from the published German application whether and or how the separation of the wort from the grain residue as proposed there can be integrated in a continuous brewing process.

Austrian Patent Specification 289,685 discloses a process in which beer sort is continuously fermented at about 10° C. The wort is fermented under pressure in a tank and the velocity of flow and the direction of flow are virtually constant in each region of the fermenting tank. The fermenting liquor which is contained in the tank consists of an emulsion of wort and carbon dioxide and has a constant composition and a constant specific gravity between 0.15 and 0.40 $g/cm^3$. This indicates an extremely high $CO_2$ content, which involves disadvantages regarding process technology and adversely affects the quality of the finished beer. In that process the rising movement in the tank is effected by an injection of $CO_2$, which has been taken from the top portion of the reactor.

German Patent Specification 41 42 646 discloses a process of producing a low-alcohol beer which contains less than 0.5% by weight alcohol and in which a first wort for making a strong beer is substantially completely fermented, the resulting product is de-alcoholized to an alcohol content below 0.5%, a second wort for making a strong beer is mixed with brew water to the original wort content of beer of normal strength, the resulting product is fermented to an alcohol content below 0.5%, and the de-alcoholized strong beer and the beer of normal strength are blended to produce a low-alcohol draft beer. German Patent specification 41 42 646 fails to disclose a continuous process of producing beer.

It is finally known to separate the alcohol from the alcohol-containing beer by flash evaporation, stripping with gases or permeation through a membrane. For instance, Published European Patent Application 0 245 845 discloses the production of non-alcoholic beers in a process in which a gas is bubbled through an alcohol-containing beer in order to desorb the alcohol and the loss of the flavor in the beer is compensated by substances which improve the flavor of the beer. Air may also be used as a gas in the known process.

It is an object of the invention to provide for the production of beer a continuous process which permits a beer of high and constant quality to be produced for a long time and permits also the continuous production of a low-alcohol beer or a non-alcoholic beer and wherein the several steps of the brewing process and of the partial or full de-alcoholization of the beer are so combined that the production costs are low.

THE INVENTION

The object underlying the invention is accomplished in that a) disintegrated and optionally malted raw materials are mashed with water and the mash is continuously fed to at least one reactor or reactor stage and is heated in steps by an indirect heat exchange and is finally heated to a temperature from 75° to 85° C., the residence time of the mash in the reactor or reactor stages is 30 to 90 minutes and the mash is held in each reactor or reactor stage at a defined temperature from 35° to 75° C., b) the grain residue is continuously removed from the mash in a decanter and is subsequently leached with the mashing water in a two-stage decanter, c) the solids-free hot wort is mixed with hops or hop extract and is continuously supplied to a flow reactor and is heated to a temperature from 105° to 140° C. and is caused to flow through said reactor for between 2 to 60 minutes and during that time is maintained at said temperature and under a gauge pressure from 1.2 to 3.6 bars, d) the pressurized wort is subjected to a flash evaporation and in a separator is continuously freed from the dregs and is subsequently cooled in a heat exchanger to the fermentation temperature, e) the cooled wort having an oxygen content from 0.5 to 3.0 mg $O_2$/l is continuously supplied to at least one fermenter, which consists of an internally recycling reactor and is operated at a temperature from 6° to 25° C. and under a pressure from 1.5 to 2 bars and in which the wort has a mean residence time from 7 to 40 hours and is continuously recycled and which contains a biocatalyst that contains a biologically active yeast, f) liquid medium is continuously withdrawn from the fermenter during the fermentation and is centrifuged to remove the free yeast cells contained therein and the liquid medium from which the yeast has been removed is heated at 50° to 90° C. for 0.5 to 30 minutes and is divided into two partial streams of hot beer, g) one martial stream of the hot beer produced in process step f) is cooled and is recycled to the fermenter, h) the second partial stream is partly or fully de-alcoholized or is cooled and filtered and after an admixing of $CO_2$ is delivered as an alcohol-containing beer.

The process in accordance with the invention can desirably be used to process malt in order to comply with the German requirement for the purity of beer, and to process other starch-containing raw materials, such as corn or sorghum. The combined use of flow reactors, decanters, biocatalysts and fluidized bed fermenters consisting of internally recycling reactors permit a continuous processing. Infections from the outside can effectively be controlled during an operation for more than 8000 hours. Specifically, the removal of the free yeast cells results in an optimum supply of nutrient to the biocatalyst and in a preservation of the long-time activity and of the structure of the biocatalyst. The process in accordance with the invention permits also an optimum utilization of raw materials and energy in conjunction with a low capital investment. It is believed that the high quality of the flavor of the beer produced by the process in accordance with the invention is particularly due to the fact that the pressure relief of the wort from which yeast has been removed and which has been heat-treated in process step d) results in a desirable removal of the diacetyl, which has been formed by the thermal converstion of alpha-acetolactate. Whereas the fermentation times are relatively short, the fermentable sugars are completely converted to alcohol so that the process in accordance with the invention can be used to produce draft beer (containing about 2.5 to 3.0% by volume alcohol) as well as stronger beers (containing about 4.5% by volume alcohol). The partial or full de-alcoholization of the beer can be effected continuously and without a loss in quality and can desirably be integrated in the continuous brewing process.

It has beer found that it will be Particularly desirable in accordance with the invention to effect the mashing of the disintegrated raw materials in process step a) in a colloid mill. A thorough mixing and a further disintegration of the mashed raw materials will be effected in the colloid mill.

The process in accordance with the invention can be carried out in a particularly desirable manner if process step c) is carried out at a temperature from 110° to 125° C. and under a pressure from 1.4 to 2.3 bars.

According to a further feature of the invention the flash evaporation in process step d) is effected in two stages and the pressure is relieved to 1 bar in the first stage and to a pressure between 0.3 and 0.7 bar in the second stage. The flash evaporation in two stages permits an optimum recovery of eat. According to the invention a supply of $CO_2$ during the flash evaporation has proved to be particularly desirable because this will expel undesired odors and flavors out of the wort before the fermentation.

In some cases it has been found that it is desirable to transfer the wort to a storage container after the dregs have been removed in process step d) and to heat the wort taken from the storage container at 60° to 100° C. for a short time before it is supplied to the heat exchanger used in step d). In that case it will be possible in case of need, e.g., during a shutdown or during cleaning operations, to store the fermentable wort for a long time and an infection of the fermenting stage by the microorganisms possibly contained in the stored wort need not be feared.

In accordance with the invention the fermentation will proceed to completion in a particularly satisfactory manner if the wort is passed through three fermenters in succession with a total residence time of 10 to 40 hours in the three fermenters. Alternatively it is possible in accordance with the invention to pass the wort through only one fermenter with a residence time of 1 to 8 hours therein. That processing has proved satisfactory in the Production of a lowalcohol beer or a non-alcoholic beer of high quality because the sugars contained in the wort are substantially fermented during the relatively short fermenting time.

In accordance with the invention it will be particularly desirable to use a biocatalyst which contains 5 to 30% by weight $TiO_2$ and comprises a biologically active yeast and a gellike matrix, the $TiO_2$ particles are between 0.1 to 1 micrometer in diameter and the catalyst is spherical. The biocatalyst affords the advantage that it can uniformly be distributed in the fluidized bed of the fermenter, has good mechanical strength properties and contains only substances which are of natural origin and/or exhibit an inert behavior in the chemical and/or biological reaction systems.

In accordance with the invention it will be desirable to heat the liquid medium from which the yeast has been removed at 60° to 65° C. for 15 to 20 minutes in process step f). That treatment will not adversely affect the flavor of the beer.

In the production of a low-alcohol beer in accordance with the invention, the second partial stream of the hot beer obtained in process step f) is divided into two parts, the alcohol is continuously removed from the first part of the hot beer by stripping with air and/or steam or by flash evaporation, the de-alcoholized beer is blended with the second part, the ratio of the rates of the first and second parts is so selected that he mixture contains less than 2.5% by volume and preferably less than 1% by volume alcohol, the hot low-alcohol beer is cooled and filtered and $CO_2$ is admixed thereto.

In the production of a non-alcoholic beer in accordance with the invention the alcohol is continuously removed from the second partial stream of the hot beer obtained in process step f) by stripping with air and/or steam or by flash evaporation, the non-alcoholic beer is cooled and filtered and $CO_2$ is admixed thereto.

It is believed that the high quality of the flavor of the beer produced by the process in accordance with the invention is particularly due to the fact that the stripping or flash evaporation results in a removal not only of the alcohol but desirably also of the diacetyl formed by the thermal conversion of alphaacetolactate whereas the flavors which are typical of the beer are preserved. For this reason there is no need for a time-consuming ripening for improving the flavor of the low-alcohol beer or of the non-alcoholic beer. Because the de-alcoholization in accordance with the invention results in a product having a very low alcohol content, the de-alcoholized beer may be mixed with an appreciable quantity of alcohol-containing beer, e.g., to produce a low-alcohol beer which contains less than 0.5% by volume alcohol and which in accordance with the German food regulations still constitutes a non-alcoholic beer. The blending effected in the process in accordance with the invention has the result that desirable flavors and odorous substances which have been formed during the brewing process enter the non-alcoholic partial stream and improve the flavor thereof.

In accordance with the invention the beer is de-alcoholized in that the alcohol is removed from the beer which s at 50° to 60° C. and this is effected in a column by a stripping with air, which is enriched with water vapor and is at a temperature from 60° to 100° C., and the non-alcoholic beer is subsequently pressure-relieved to 1 bar. That Processing results in a substantially complete removal of the alcohol substantially without a change of the flavor of the beer. 3 to 6 sm$^3$ (sm$^3$=standard cubic meter) of air per liter of beer are preferably used to remove the alcohol from the beer. The water vapor content of the air as preferably about 85 to 95% of the saturation concentration at the temperature of the air leaving the stripper. The stripping does not result in an appreciable loss of desirable odorous substances and flavors.

In accordance with the invention it is desirable in some cases to supply the cooled non-alcoholic beer produced in process step g) to a fermenter, which consists of an internally recycling reactor and is operated at a temperature from 0° to 6° C. and under a pressure from 1.2 to 1.5 bars and in which the non-alcoholic beer has a residence time of 0.2 to 2 hours and contains a biocatalyst which is identical to the biocatalyst used in process step e). That after-fermentation of the non-alcoholic beer at a low temperature does not appreciably increase the alcohol content and the after-fermentation may further improve the flavor of the low-alcohol beer or the non-alcoholic beer.

Figure 2:
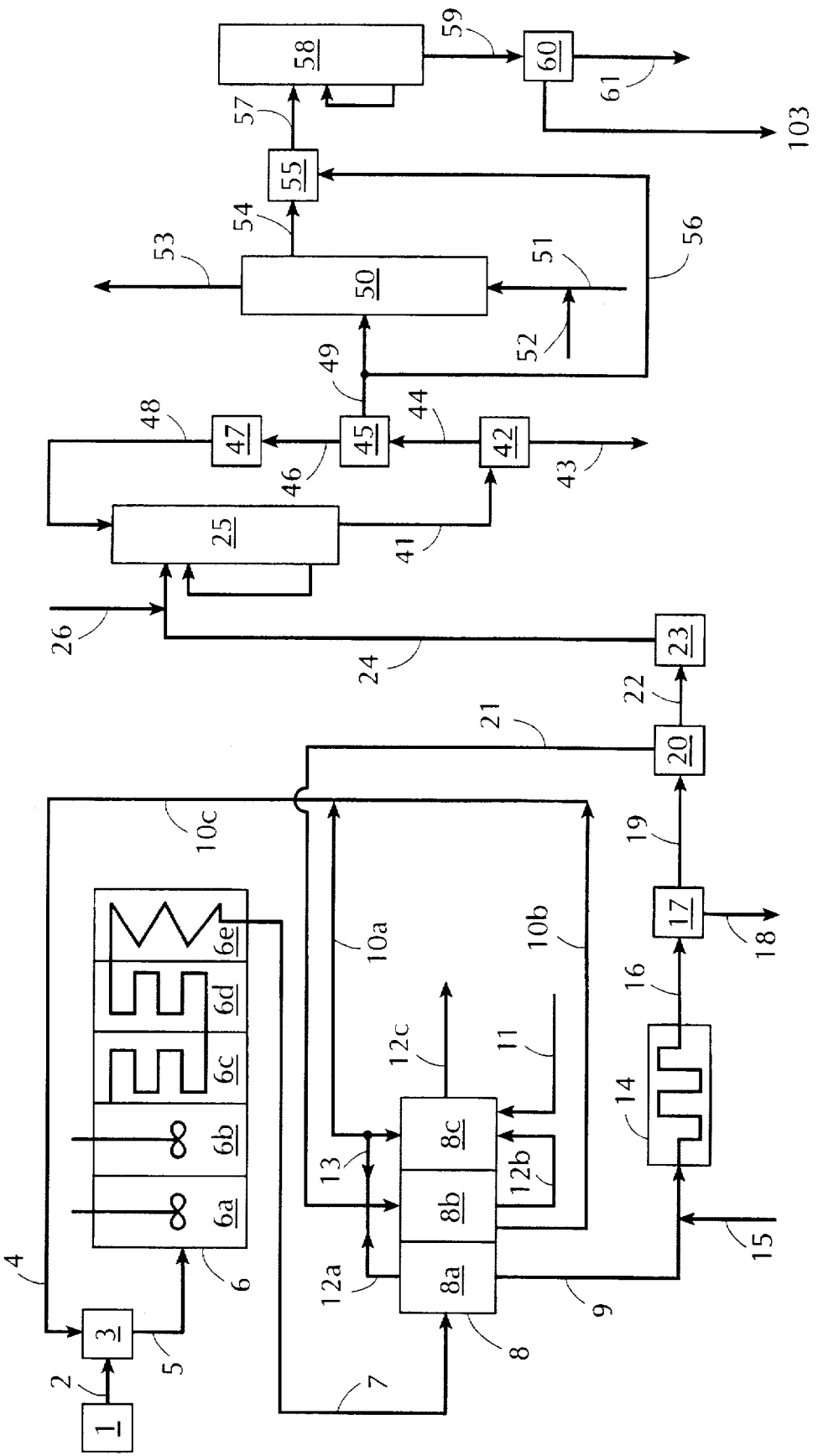

The invention will be explained in more detail hereinafter with reference to the process flow schemes shown in the drawing, in which FIG. 1 illustrates a process of producing a strong beer which contains about 4.5% by volume alcohol, FIG. 2 illustrates a process of producing a low-alcohol beer which contains about 0.5% by volume alcohol, and FIG. 3 illustrates a process of Producing a non-alcoholic beer which contains about 0.05% by volume alcohol.

In all three variants of the process, brewer's barley is moistened and is germinated at a temperature from 15° to 18° C. within 8 days to form green malt. The green malt is air-dried and is subsequently kiln-dried on trays at 50° to 18° C. Germs and dust are removed from the resulting kiln-dried malt, which is then crushed. Germinating and kiln drying result in a formation of native hydrolytic enzymes, by which the starch contained in the brewer's barley is partly saccharified. The operations described thus far are not represented in the process flow schemes.

The strong beer is produced as follows by the process illustrated in FIG. 1.

The crushed malt is continuously conveyed from the supply bin 1 through the duct 2 into the colloid mill 3, which is also continuously supplied through line 4 with mashing water. In the colloid mill 3 the crushed malt is re-disintegrated and is intensely mixed with the mashing water at the same time. The mashing water is conducted in line 4 and is at a temperature of about 35° C. so that the mash is at a temperature of 35° C. as it leaves the colloid mill.

Through line 5 the mash is continuously supplied to the reactor system 6, which consists of the two stirred reactors 6a and 6b, the two flow reactors 6c and 6d and the heat exchanger 6e. The mash is at a temperature of 35° C. at the inlet of the reactor system 6 and in the stirred reactor 6a is held at that temperature for about 20 minutes. The mash then flows into the stirred reactor 6b and is kept therein at a temperature of 50° C. for about 20 minutes (protease rest). In the flow reactor 6c the mash is kept at a temperature of 63° C. for 16 minutes (beta-amylase rest) and this is succeeded in the flow reactor 6d by the alpha-amylase rest at 73° C. for 8 minutes. In the succeeding heat exchanger 6e the mash is heated to 76° to 78° C. to inactivate the enzymes. The several units of the reactor system 6 permit defined temperatures to be maintained for defined rest times. Each reactor is preceded by a heat exchanger for bringing the mash to the temperature to be maintained for the rest time. Said heat exchangers are not shown in the drawing.

The mash is continuously withdrawn from the reactor system 6 and is fed through line 7 to a three-stage decanter 8, in which a solid-liquid separation is effected by centrifugation. The grain residue is removed in the First decanter stage 8a and is fed in line 12a to the second decanter stage 8b, in which the grain residue is leached by means of a partial stream of the effluent from the third decanter stage 8c. That partial stream is fed to the second decanter stage 8b through line 13. The leached grain residue is fed from the second decanter stage 8b through line 12b to the third decanter stage 8c and is leached therein once more. The leaching in the third decanter stage 8c is effected with water, which is supplied to the third decanter stage 8c in line 11. The effluent from the second decanter stage 8b and that partial stream of the effluent from the third decanter stage 8c which is not used for leaching are fed in lines 10a, 10b, and 10c to line 4 so that both streams are used as mashing water. The grain residue which has been leached twice and comes from the third decanter stage 8c is discharged through the duct 12c.

The solids-free hot wort is continuously conveyed from the line 9 to the flow reactor 14. Which consists of a heatable tube reactor, and is boiled therein at 115° C. for about 30 minutes. A pressure of about 1.7 is maintained during the boiling. Before the wort enters the flow reactor 14, hop extract proportioned through the duct 15 is added to the wort. The boiling of the hopped wort results in an isomerization of substances contained in the hop extract and in a coagulation of proteins.

The pressurized wort is continuously conveyed in line 16 from the flow reactor 14 into the flash evaporator 17, in which a cooling and a pressure relief to 1 bar (atmospheric pressure) are effected. The aqueous condensate flows through line 18 to the sewer and the wort is continuously conveyed through line 19 to the separator 20, in which the dregs are removed, which are discharged in duct 21. For a utilization of soluble substances contained in the dregs, the latter are supplied to the second decanter stage 8b and are leached therein. The solids-free wort is then supplied through line 22 to the heat exchanger 23 and is cooled therein to the fermentation temperature of 16° C. The cooled wort leaving the heat exchanger 23 may be supplied to a storage container. The storage container serves to receive during the cleaning of the fermenter system the wort which comes continuously from the units which contain the hot wort, and continuously to supply wort to the fermenter system during the cleaning of the units which contain the hot wort. The storage container may be succeeded by a short-time heater, in which the wort is sterilized by being heated. The storage container and the short-time heater are not shown in the drawing.

From the heat exchanger 23 the cooled wort flows through line 24 continuously to the fermenter system, which consists of three fermenters 25a, 25b, and 25c. Each fermenter is operated as an internally recycling reactor, in which the wort is internally recycled and the ratio of the supply rate to the recycling rate is between 1:30 and 1:80. The reaction zone of each fermenter contains a biocatalyst, Which is kept in a fluidized state by the circulating wort. Each fermenter is operated under a pressure of about 1.8 bars. The cooled wort entering the first fermenter is mixed in line 24 with air to have an oxygen content of 1.5 mg $O_2$/liter of wort. The air is supplied through line 26. The residence time of the liquid medium in each fermenter is about 10 hours so that the total fermentation time amounts to 30 hours. During that time the fermentable sugars are almost entirely converted to alcohol and $CO_2$. The alcohol content of the resulting beer is defined by the extract content and by the degree of fermentation. Owing to its high mechanical strength and its optimum behavior in a fluidized bed, the catalyst described in German Patent Specification 3,704,48 has proved to be most desirable as a biocatalyst.

In some cases it will be desirable to supply to each fermenter a partial stream of the oxygen-containing cooled wort which is conducted in line 24. The ratio of the rates of the three partial streams is 75:15:10 so that 10% of the wort are supplied to the third fermenter. That processing permits a satisfactory operation of the fermenters but is not shown in the drawing.

During the fermentation, yeast cells are formed which are not immobilized in the biocatalyst but together with the liquid medium form a suspension. The free yeast cells are desirably removed from the contents of each fermenter by the centrifugation of a partial stream. For that purpose a partial stream is removed from each fermenter 25a, 25b and 25c through a line 27a, 27b, and 27c and is conducted through the centrifuge 40 and then recycled through a line 28a, 28b and 28c to the associated fermenter. The effluent from the last fermenter 25c is continuously supplied in line 29 to the centrifuge 30 for a separation of any free yeast cells which are present. The yeast cells are removed from the centrifuge 30; through line 102 and from centrifuge 40 through line 100 as shown in FIG. 1 The removal of free yeast cells by the centrifugation in the centrifuge 30 results also in a significant improvement of the subsequent filtration of the beer.

The fermented liquid medium is conducted through line 31 to the flow reactor 32 and is heated therein at 65° C. for 15 minutes. The flow reactor 32 communicates through line 33 with the flash evaporator 34, n which the pressure is relieved to 1 bar (atmospheric pressure). The aqueous condensate from the flash evaporator 34 is delivered through line 35 into the sewer and the beer is conducted through line 36 to the eat exchanger 37 and is cooled therein to about 15° C. A partial stream of the beer leaving the heat exchanger 37 is fed to the fermenter 25a through line 38. The second partial stream leaves the heat exchanger 37 as a final product in line 39. In case of need, the effluent which is conducted from the heat exchanger 37 in line 39 may be filtered. That process step is not shown in the drawing.

The low-alcohol beer is produced as follows by the process illustrated in FIG. 2.

The solids-free wort is produced by the partial process which is illustrated in FIG. 1 and has been described hereinbefore and is cooled in the heat exchanger 23 to the fermentation temperature of 16° C. From the heat exchanger 23 the cooled wort flows through line 24 continuously to the fermenter 25, which consists of an internally recycling reactor, in which wort is internally recycled and the ratio of the supply rate to the recycling rate is between 1:30 and 1:80. The reaction zone of he fermenter 25 contains a biocatalyst, which is kept in fluidized state by the circulating wort. The fermenter 25 is operated at a temperature of 16° C. and under a pressure of about 1.8 bars. The cooled wort entering the fermenter 25 is mixed in line 24 with air to have an oxygen content of 1.5 mg $O_2$/liter of wort. The air is supplied through line 26. The residence time of the liquid medium in the fermenter 25 is about 5 hours. During that time the major part of the fermentable sugars is converted to alcohol. Owing to its high mechanical strength and its optimum behavior in a fluidized bed, the catalyst described in German Patent Specification 3,704,478 has proved to be most desirable as a biocatalyst.

The liquid medium is continuously removed from the fermenter 25 and is supplied in line 41 to the separator 42, in which the free yeast cells formed in the fermenter 25 are removed. The yeast removed by centrifugation is discharged through line 43. The solids-free liquid medium is supplied in line 44 to the heat exchanger 45 and is heated therein to a temperature of 62° C. The residence time of the medium in the heat exchanger 45 is about 20 minutes. A partial stream of the effluent from the heat exchanger 45 is fed in line 46 to the heat exchanger 47 and is cooled therein to the fermentation temperature and is recycled in line 48 to the fermenter 25.

The second partial stream of the effluent of the heat exchanger 45, i.e., the hot beer is divided in two parts. The first part flows in line 49 to the stripping column 50, which is operated at a mean operating temperature of 52° C. The stripping column 50 is supplied via line 51 with air, Which has a temperature of 70° C. and a water content amounting to 92% of the saturation water content at the air exit temperature. That air is supplied to the stripping column 33 at a rate of 4 $sm^3$ per liter of beer. To control the water content of the air, steam is supplied in line 52 into line 51. The residence time of the beer in the stripping column 50 is 12 minutes. The air stream is withdrawn from the stripping column 50 through line 53. The condensible components, particularly alcohol and water, may be removed from the air stream in a condenser, which is not shown in the drawing.

The de-alcoholized product which leaves the stripping column 50 through line 54 is pressure-relieved to atmospheric pressure (1 bar) and in the heat exchanger 55 is cooled to a temperature of 2° C. Through line 56 the heat exchanger 55 is supplied also with the second part of the hot beer coming from the heat exchanger 45. That part is also cooled in the heat exchanger 55 to a temperature of 2° C. The ratio of the rates of the two parts, which leave the heat exchanger 45 through the lines 49 and 56, is so selected that an alcohol content below 0.5% by volume results.

The effluent from the heat exchanger 55 flows in line 57 to the fermenter 58, which is operated as an internally recycling reactor, which contains the same biocatalyst as the fermenter 25 and is operated at a temperature of 2° C. and under a pressure of about 1.4 bars. The residence time of the low-alcohol product in the fermenter 58 is 1 hour, in which the flavor is improved but the alcohol content of the product is not increased. The effluent from the fermenter 58 supplied in line 59 to a filter 60, which may be operated with a filter aid and in which dregs and any free yeast cells are separated from the low-alcohol beer. The low-alcohol beer contains less than 0.5% by volume alcohol and leaves the filter 60 through the line 61, in which $CO_2$ may be admixed. The filtered out material is removed through line 103 (FIG. 2).

The non-alcoholic beer is produced as follows by the process illustrated in FIG. 3:

The solids-free wort is produced by the partial process which is illustrated in FIG. 1 and has been described hereinbefore and is cooled in the heat exchanger 23 to the fermentation temperature of 16° C. From the heat exchanger 23 the cooled wort flows through line 24 continuously to the fermenter as in the process which is illustrated in FIG. 2 and has been described hereinbefore. In the fermenter 25 a major part of the fermentable sugars is converted to alcohol. As in the process illustrated in FIG. 2 and described hereinbefore the liquid medium is continuously withdrawn from fermenter 25 and after being processed is recycled to the fermenter 25.

In the process illustrated in FIG. 3 the entire second partial stream of the effluent from the heat exchanger 45, i.e., the hot beer flows in line 49 to the stripping column 50, which is operated at a mean operating temperature of 52° C. The stripping column 50 is supplied via line 51 with air, which has a temperature of 70° C. and a water content amounting to 92% of the saturation water content at the air exit temperature. That air is supplied to the stripping column 33 at a rate of 4 sm³ per liter of beer. To control the water content of the air, steam is supplied in line 52 into line 51. The residence time of the beer in the stripping column 50 is 12 minutes. The air stream is withdrawn from the stripping column 50 through line 53. The condensible components, particularly alcohol and water, may be removed from the air stream in a condenser, which is not shown in the drawing.

The de-alcoholized product which leaves the stripping column 50 through line 62 is mixed with $CO_2$ and is subsequently pressure-relieved and in the heat exchanger 63 is cooled to a temperature of 3° C. The cooled product is discharged in line 64 and is Processed further in the usual manner. The non-alcoholic beer has an alcohol content below 0.05% by volume.

It will be understood that the specification and examples are illustrative but not limitative of the present invention and that other embodiments within the spirit and scope of the invention will suggest themselves to those skilled in the art.

We claim:

1. A continuous process for producing beer, comprising
   a) (i) mashing disintegrated, optionally malted, raw materials with water to form a mash;
   (ii) continuously feeding the mash to at least one reactor or reactor stage, the mash being held in said least one reactor or reactor stage at a defined temperature from 35° to 75° C. said mash being heated in steps by an indirect heat exchange to a temperature of from 75° to 85° C., the mash having a residence time in the least one reactor or reactor stage of 30 to 90 minutes;
   b) separating a grain residue from the mash to produce a solids-free hot wort;
   c) (i) mixing the solids-free hot wort with hops or hop extract to form a mixture;
   (ii) continuously supplying the mixture to a flow reactor wherein the mixture is heated and is caused to flow through said flow reactor for between 2 to 60 minutes while the mixture is at a temperature of from 105° to 140° C. and under a gauge pressure of from 1.2 to 3.6 bars;
   d) (i) subjecting the pressurized wort to a flash evaporation;
   (ii) continuously separating the wort from the dregs;
   (iii) cooling the wort to a fermentation temperature;
   e) fermenting the cooled wort having an oxygen content from 0.5 to 3.0 mg $O_2$/l in at least one fermenter which contains a biocatalyst that contains a biologically active yeast;
   f) (i) withdrawing a liquid medium from the fermenter during the fermentation;
   (ii) removing the free yeast cells contained therein;
   (iii) heating the liquid medium from which the yeast has been removed to a temperature of from 50° to 90° C. for 0.5 to 30 minutes;
   (iv) dividing the heated liquid medium into first and second partial streams of hot beer;
   g) (i) cooling the first partial stream of the hot beer;
   (ii) recycling the cooled stream to the fermenter; and
   h) processing the second partial stream to form a beer.

2. The process of claim 1 wherein the second partial stream is cooled and filtered and after an admixing of $CO_2$ forms an alcohol-containing beer.

3. The process of claim 1 wherein the second partial stream is partly or fully de-alcoholized.

4. The process of claim 1 wherein the mashing of the disintegrated raw materials is effected in a colloid mill.

5. The process of claim 1 wherein step c)(ii) is carried out at a temperature from 110° to 125° C. and under a pressure from 1.4 to 2.3 bars.

6. The process of claim 1 wherein the flash evaporation in step d)(i) is performed in two stages and the pressure is relieved to 1 bar in the first stage and to between 0.3 and 0.7 bar in the second stage.

7. The process of claim 1 wherein $CO_2$ is supplied during the flash evaporation in step (d)(i).

8. The process of claim 1 wherein the wort is transferred to a container after the dregs have been removed in step d) (ii) and the wort taken from the container is heated to 60° to 100° C. for a short time before it cools to the fermentation temperature.

9. The process of claim 1 wherein the cooled wort is passed through three fermenters in succession with a total residence time of 10 to 40 hours in the fermenters.

10. The process of claim 1 wherein the cooled wort is passed through a fermenter with a residence time of 1 to 8 hours therein.

11. The process of claim 1 wherein the biocatalyst is spherical and comprises 5 to 30% by weight of $TiO_2$ particles having a diameter of from 0.1 to 1 micrometers, a biologically active yeast, and a gellike matrix.

12. The process of claim 1 wherein in the process step (f) the liquid medium from which the yeast has been removed is heated at 60° to 65° C. for 15 to 20 minutes.

13. The process of claim 1 wherein the grain residue is removed from the mash in a decanter and is subsequently leached with the mashing water in a two-stage decanter.

14. The process of claim 1 wherein the least one fermenter is an internally recycling reactor and is operated at a temperature of from 6° to 25° C. and at a pressure of from 1.5 to 2 bars and in which the wort has a mean residence time from 1 to 40 hours and is continuously recycled.

15. The process of claim 1 wherein the second partial stream of the hot beer is divided into two parts, the alcohol is continuously removed from the first part of the hot beer by stripping with air and/or steam or by flash evaporation to form a de-alcoholized beer, the de-alcoholized beer is blended with the second part to form a low-alcohol beer, the ratio of the rates of the first and second parts is so selected that the mixture contains less than 2.5% by volume of alcohol, and the hot low-alcohol beer is cooled and filtered and $CO_2$ is admixed thereto.

16. The process of claim 1 wherein the alcohol is continuously removed from the second partial stream of the hot beer obtained in step (f) by stripping with air and/or steam or by flash evaporation to form a substantially non-alcoholic beer, and the non-alcoholic beer is cooled, filtered and $CO_2$ is admixed thereto.

17. The process of claim 15 wherein the alcohol is removed from the hot beer, which is at 50° to 60° C., in a column by a stripping with air enriched with water vapor and is at a temperature of from 60° to 100° C. to form a substantially non-alcoholic beer, and the nonalcoholic beer is subsequently pressure-relieved to 1 bar.

18. The process of claim 16 wherein the alcohol is removed from the hot beer, which is at 50° to 60° C., in a column by a stripping with air enriched with water vapor and is at a temperature of from 60° to 100° C., and the non-alcoholic beer is subsequently pressure-relieved to 1 bar.

19. The process of claim 15 wherein the cooled low-alcohol beer is introduced into a fermenter which consists of an internally recycling reactor and is operated at a temperature from 0° to 6° C. and at a pressure of from 1.2 to 1.5 bars and in which the non-alcoholic beer has a residence time of from 0.2 to 2 hours and contains a biocatalyst which is of the identical type to the biocatalyst used in step (e).

20. The process of claim 16 wherein the cooled low-alcohol beer or non-alcoholic beer is introduced into a fermenter which consists of an internally recycling reactor and is operated at a temperature from 0° to 6° C. and at a pressure of from 1.2 to 1.5 bars and in which the non-alcoholic beer has a residence time of from 0.2 to 2 hours and contains a biocatalyst which is of the identical type to the biocatalyst used in step (e).

21. The process of claim 15 wherein the rates of the first and second parts are so selected that the mixture contains less than 1% by volume of alcohol.

22. The process of claim 17 wherein the substantially non-alcoholic beer is introduced into a fermenter which consists of an internally recycling reactor and is operated at a temperature from 0° to 6° C. and at a pressure of from 1.2 to 1.5 bars and in which the non-alcoholic beer has a residence time of from 0.2 to 2 hours and contains a biocatalyst.

* * * * *